United States Patent
Lasner et al.

(10) Patent No.: US 7,497,867 B2
(45) Date of Patent: Mar. 3, 2009

(54) HANDLES AND SHAFTS FOR MANUALLY ADJUSTABLE SCISSORS AND FORCEPS

(76) Inventors: Jeffrey Lasner, 4 Baltusrol Dr., Purchase, NY (US) 10577; Michael Lasner, 33 Barker Ave., White Plains, NY (US) 10601

( * ) Notice: Subject to any disclaimer, the term of this patent is extended or adjusted under 35 U.S.C. 154(b) by 961 days.

(21) Appl. No.: 10/889,342

(22) Filed: Jul. 12, 2004

(65) Prior Publication Data
US 2006/0009795 A1    Jan. 12, 2006

(51) Int. Cl.
    *A61B 17/28*    (2006.01)
(52) U.S. Cl. ...................................................... 606/174
(58) Field of Classification Search ................. 606/170, 606/174, 176, 205–210, 151, 158; 30/135, 30/134, 234, 235, 261, 266
See application file for complete search history.

(56) References Cited

U.S. PATENT DOCUMENTS

| | | | | |
|---|---|---|---|---|
| 4,527,331 A | * | 7/1985 | Lasner et al. | ............... 606/174 |
| 5,813,417 A | * | 9/1998 | Rudolph | ...................... 30/261 |
| 6,592,603 B2 | * | 7/2003 | Lasner | ....................... 606/174 |

* cited by examiner

*Primary Examiner*—Kevin T Truong
(74) *Attorney, Agent, or Firm*—Alfred E. Miller (57) ABSTRACT

A surgical scissors or forceps for use where the operative field is greatly reduced and the instrument is elongated with a low profile and having convexity of the shanks in order to measurably increase the beam strength of the device. The instrument is further provided with interchangeable handle inserts that provide additional weight at the back end of the instrument.

11 Claims, 10 Drawing Sheets

HANDLES AND SHAFTS FOR MANUALLY ADJUSTABLE SCISSORS AND FORCEPS

The present invention is directed to scissors and forceps of the type generally used for surgical medical and dental procedures. Instruments of this type are shown and described in my U.S. Pat. No. 6,592,603 issued on Jul. 15, 2003.

While the instruments shown and described in the above-mentioned patent are in the order of 5½ inches in overall length and have considerable bulk, especially at the working end of the instrument there is a need for surgical instruments with both reduced bulk as well as longer length when performing more delicate medical and dental procedures where the openings or operative fields are greatly reduced. An example may be the use of neurosurgical or cardiovascular scissors, which may be as long as 10 or 12 inches. In that case it is necessary to reduce the bulk of the instruments so that the surgeon can easily manipulate the scissors or forceps in tight openings in order to properly perform the procedure.

It was noted that when the length of the surgical instrument is increased to 7 inches and greater that the flexibility of the flat handle and shanks combined with the increased length caused a flexing of the handle upon closure which prevents the entire force applied at the handle to be completely transmitted to the blades of the scissor resulting in incomplete closure. This was not the case with the shorter 5½-inch instrument because of the relatively short length the entire force applied at the handle is transmitted to the blades resulting in complete closure of the device.

However, when increasing the length of the scissors or forceps with narrower flat shanks and handles the force applied at the handle results in less force at the working end of the instrument, so that the scissors will not close completely and the forceps will not have the necessary grasping force.

Consequently, it is necessary to create beam strength in the shank portions of the instruments, as well as in the handle. With added beam strength the amount of force exerted on the handles of the instrument will be transferred to the cutting blades so that the blades will close in cutting fashion. The forceps, with added beam strength, will close with strong gripping action. Thus, the longer surgical instruments are capable of transmitting the entire force applied at the handle to the blades, ensuring complete closure.

In order to overcome the problem set forth above the beam strength has been increased in the shank and handle portions by making a convexity in one or both of those portions. The amount of convexity for the shank portion can be different from the convexity of the handle portion.

In the past surgical scissors and forceps were fabricated by the steel being machined out of metal stock or drop forged. It is a principal feature of this invention to manufacture surgical scissors and forceps by stamping heat treatable or non-heat treatable steel with a procedure that creates a convexity in the shanks and handles of surgical instruments. Thus, the new method of manufacture results in a lightweight instrument with sufficient beam strength in an elongated scissors so that the entire force exerted at the end having the handle to the blades ensures complete closure of the blades at the other end of the instrument.

It should also be noted that it is much more economical to manufacture a surgical instrument by stamping than those instruments being produced by machining or drop forging.

Furthermore, the present surgical instruments may be made from heat treatable, as well as non-heat treatable materials, such as stainless steel. A manufacturing benefit is derived by fabricating the present instrument out of softer, heat treatable steel, and then heat treating to harden. In this procedure the heat treatable steel starts out much softer and is therefore easier to create the necessary curvatures in die shanks to create the optimum beam strength and later heating to harden the instrument. On the other hand, the instrument can be fabricated of non-heatable steel. But the metal stock is more difficult to bend efficiently and consistently.

The above and other features of the invention will be apparent by reference to the following description of the invention and drawings.

DESCRIPTION OF THE PREFERRED EMBODIMENTS

Figure 1:
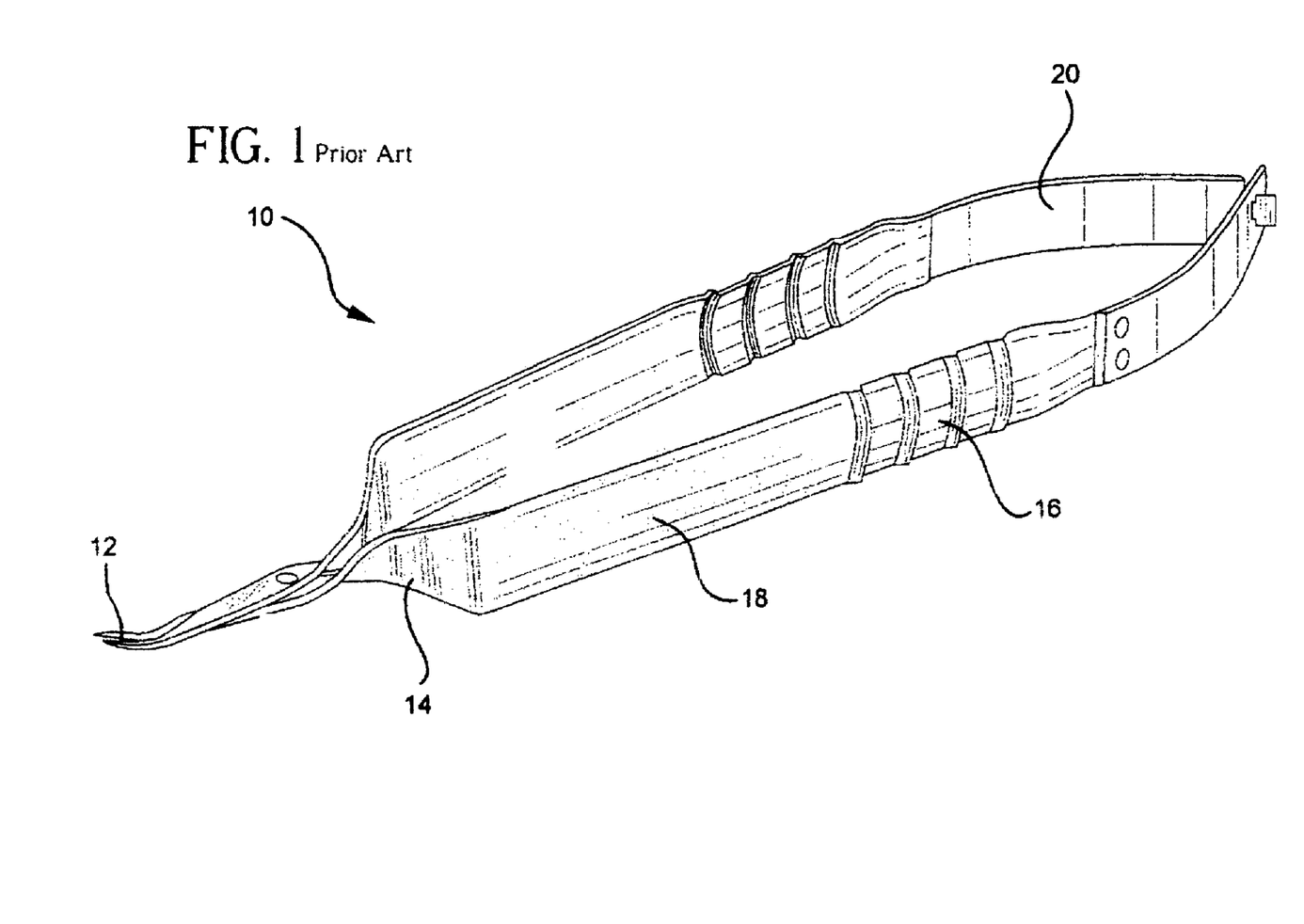
FIG. 1 is a perspective view of a surgical scissors showing a prior art construction.
Figure 2:
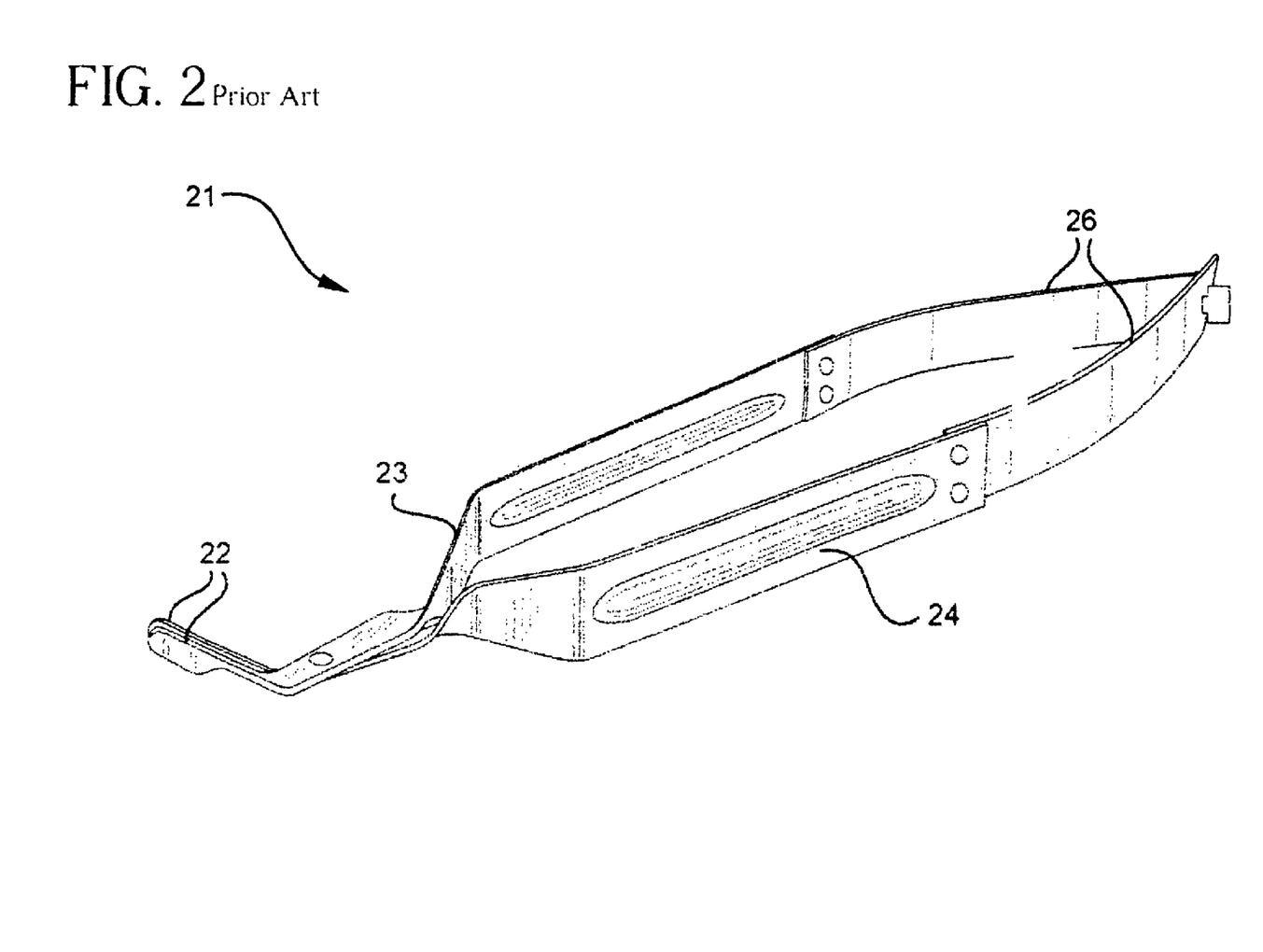
FIG. 2 is a perspective view of a surgical forceps showing a prior art construction.

FIGS. 1 and 2 of the drawings show examples of prior art construction in which FIG. 1 is a surgical scissors and FIG. 2 is a surgical forceps. It should be noted that in FIG. 1 the scissors is referred to generally by the reference numeral 10 and is provided with cutting blades 12 and 14, handle parts or portion 16, and flat portions 18 between the shanks and handle. Interlocking flexible bands 20 are connected to the ends of the handle 16. The handle parts 16 have a convexity to add beam strength to the surgical device. As seen in FIG. 2 the forceps are provided with gripping platforms 22, a handle 24 and interlocking flexible bands 26, whereby the handle is relatively flat. The above surgical scissors and forceps are utilized when the openings and operative field is large, and therefore a relatively short length is appropriate for certain procedures in dentistry as well as in other oral surgery.

However, in more delicate dental and medical procedures, where the openings or operative field are greatly reduced an elongated and narrow instrument is needed to address the reduced field of operation for the surgeon. The problem would not be solved by merely reducing the bulkiness of the prior art surgical instruments, but the construction of the new sleek instrument should be such that the total effective force at the handle would be transmitted to the cutting blades or the platforms of the forceps surgical devices.

In the case of neurosurgical and cardiovascular scissors the length may be extended to 10-12 inches. Consequently it is important that the same applied force exerted at the handles appears without being diminished at the blades of the scissors.

Figure 3:
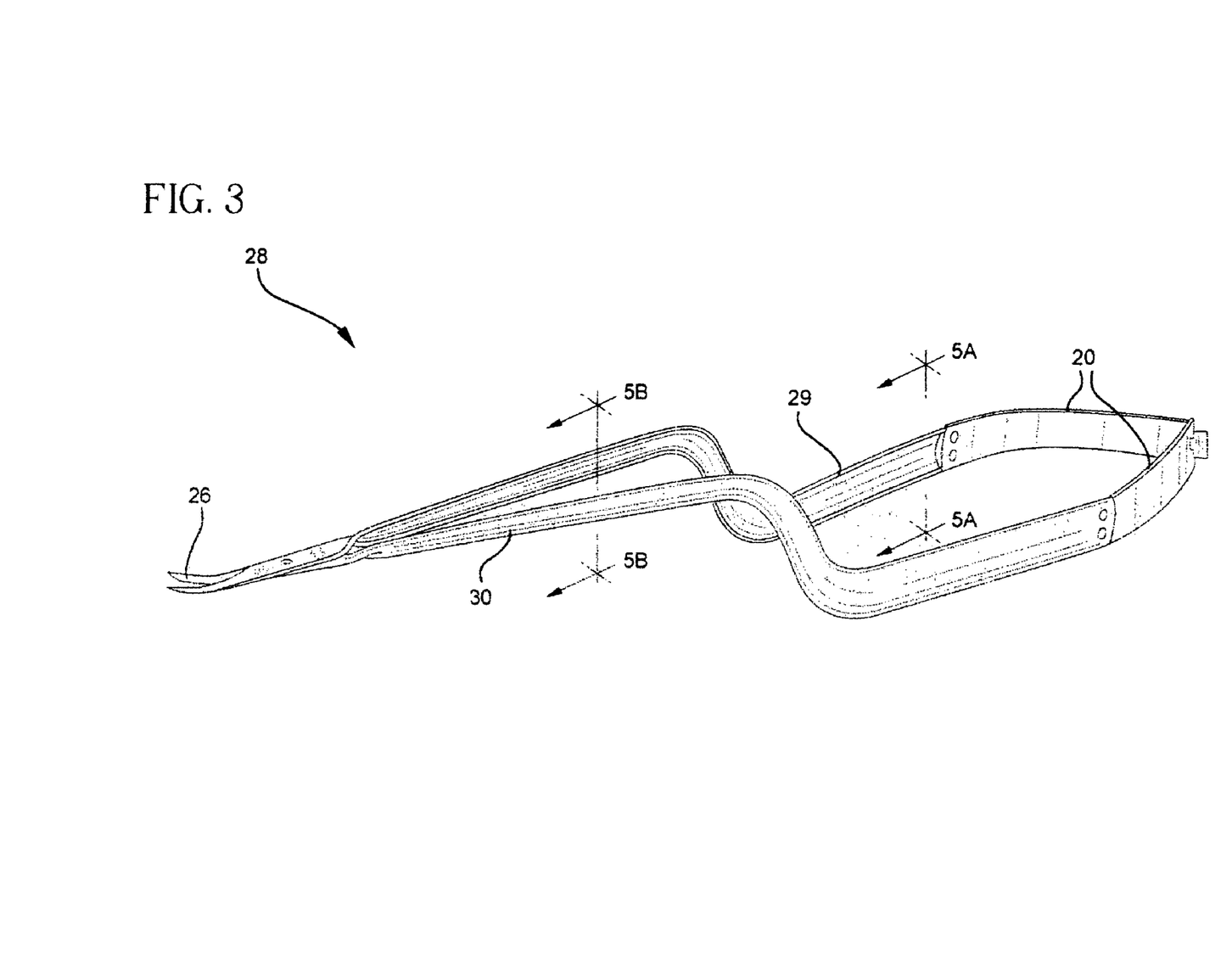
FIG. 3 is a perspective view of a surgical scissors constructed according to the teachings of my invention.
Figure 4:
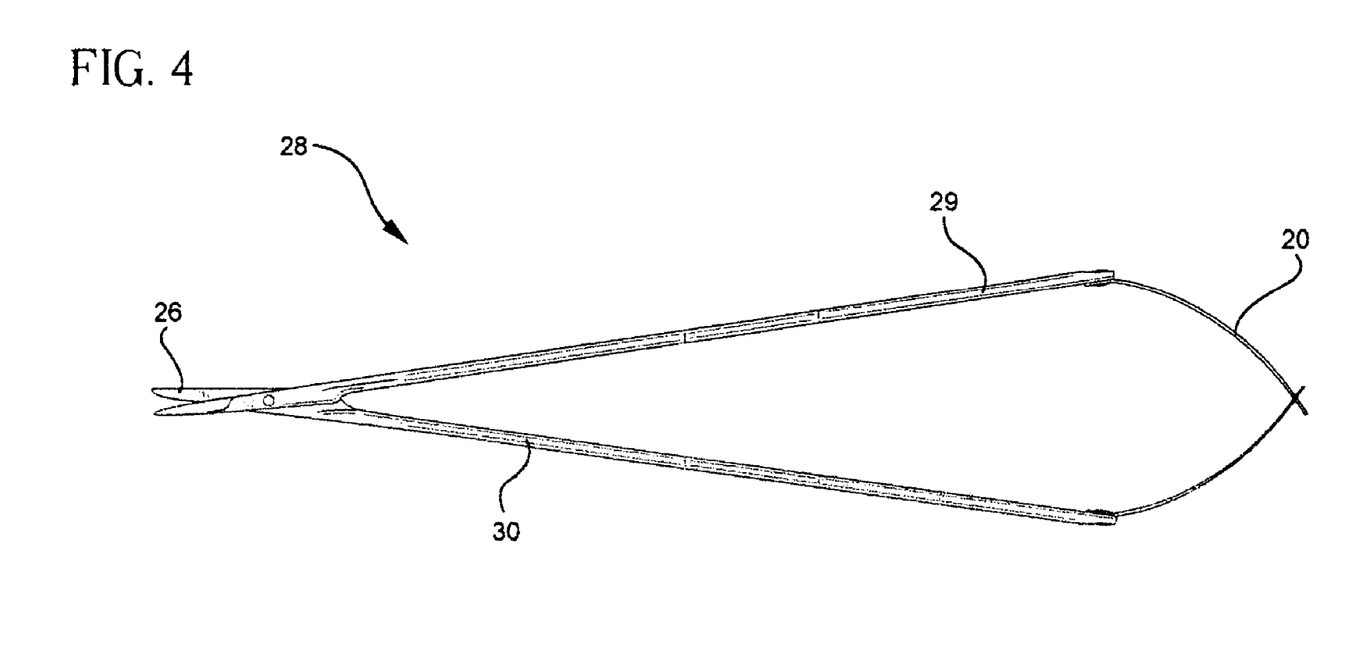
FIG. 4 is a top plan view of the improved surgical scissors.
Figure 5A:
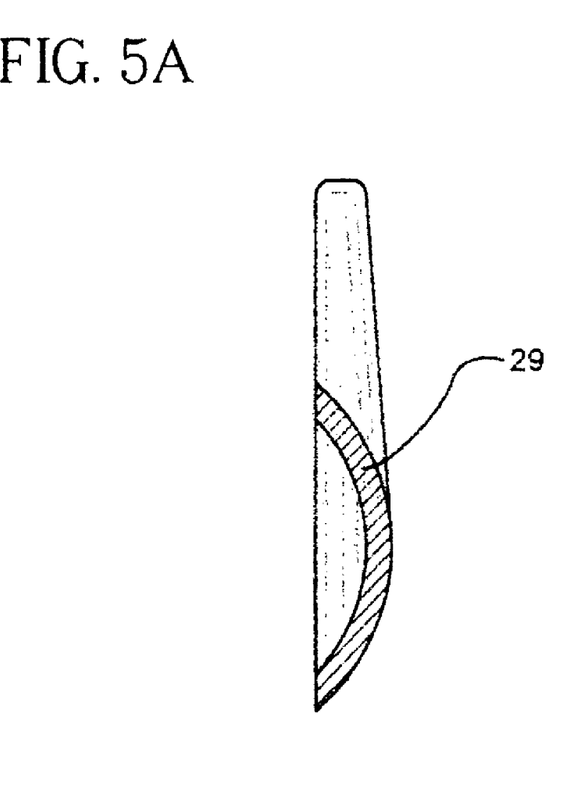
FIG. 5 is a sectional view taken along 5-5 of FIG. 3.

As seen in FIGS. 3 and 4 the improved surgical scissors is shown constructed of a medical grade flexibly resilient material in which the handle parts portions can be either flat, or slightly convex, as shown in FIG. 5a. However, in order to create sufficient beam strength in the elongated instrument, referred to generally by the reference numeral 28, the bulk has been considerably reduced and the shank portions 30 have a much greater curvature than that of the handle parts 29. The shank parts may have any curvature, but it is preferable to have at least a 180° curvature. The curvature of the shank portion 30 may be either convex or concave to add beam strength to the instrument, however a convex curvature is preferred since the important feature of the invention which is being a low profile surgical instrument, is preserved by that construction.

The present scissors and forceps are preferably manufactured of a heat treatable material, such as stainless steel, although the devices can be fabricated with relative hard non-treatable material, but it is difficult to bend that material and get consistent results. The softer, heat treatable material can be easier to bend the shanks of the instruments, which are then heat treated to harden the material.

Figure 5B:
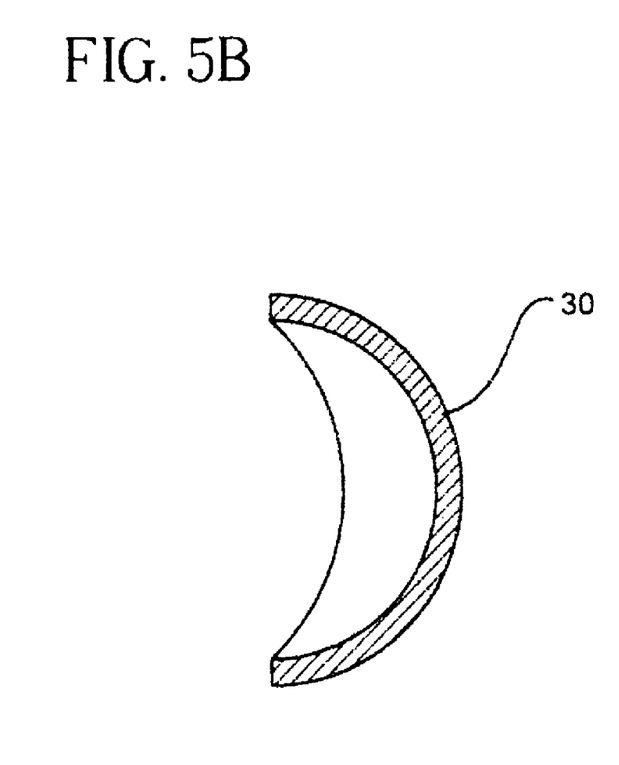

As seen in FIGS. 5a and 5b the convexity of the shanks portions of the surgical cutting instrument is much greater than the convexity of the handle portion in order to increase the beam strength of the elongated and lower profiled instrument.

Figure 6:
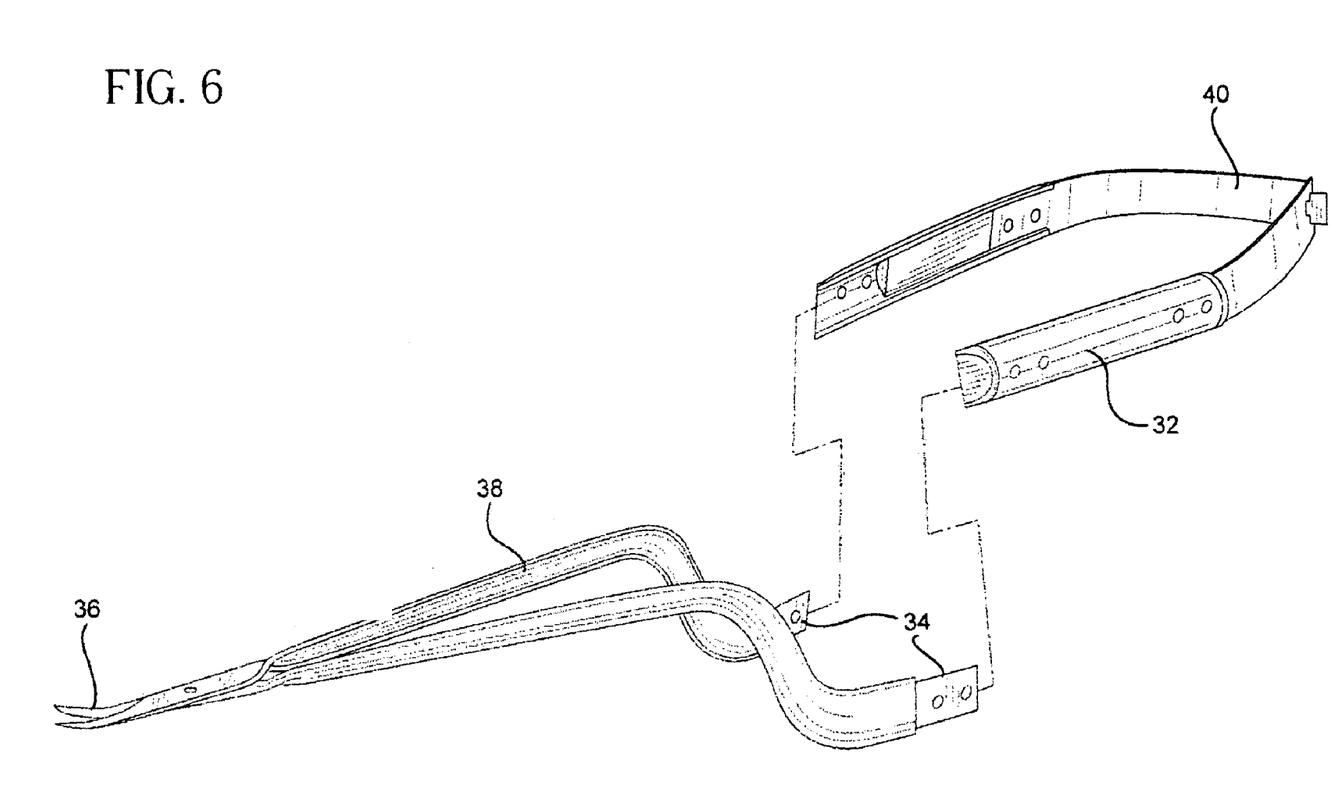
FIG. 6 is an exploded view of an alternate embodiment of the present invention in which a separate handle portion is attached to a flat connecting part between the shanks of the scissors and the interconnected band portion.
Figure 7:
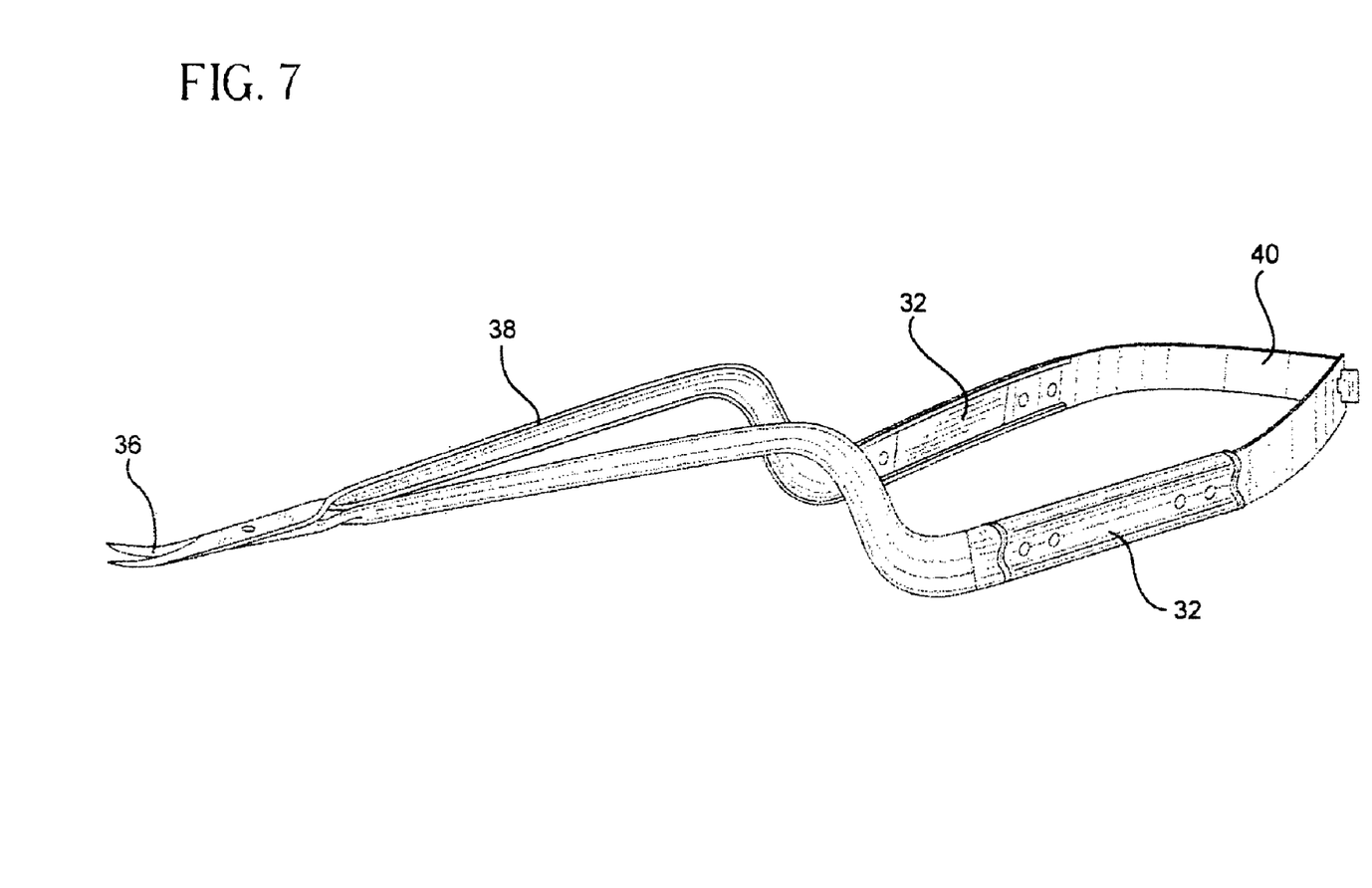
FIG. 7 is a perspective view of the complete assembly shown in FIG. 6.

FIGS. 6 and 7 is an alternate embodiment of the present invention having handle insert parts 32 attached to a flat connecting piece 34. The handle has a rounded or convex gripping surface. The instrument has cutting blades 36, shanks 38, and interconnecting flexible bands 40.

The handle inserts are shown as convex, and may be of any convexity required by the operating surgeon who desires to roll his or her fingers on the handle parts 32 when performing surgical procedures. However, if the operating surgeon requires different handle parts, such as concave handle inserts, he or she may attach the concave handles to the flat connecting pieces 34 for positive gripping. The handle inserts add increased weight at the back end of the handle portion of the surgical instrument so that the user can more easily operate the cutting blades or forceps at the forward part of the instrument. In addition, it should be noted that another benefit of the arrangement is the ability to have an inventory of various pre-made handle inserts, which can be easily stored and inserted upon receiving a specific order.

Figure 8:
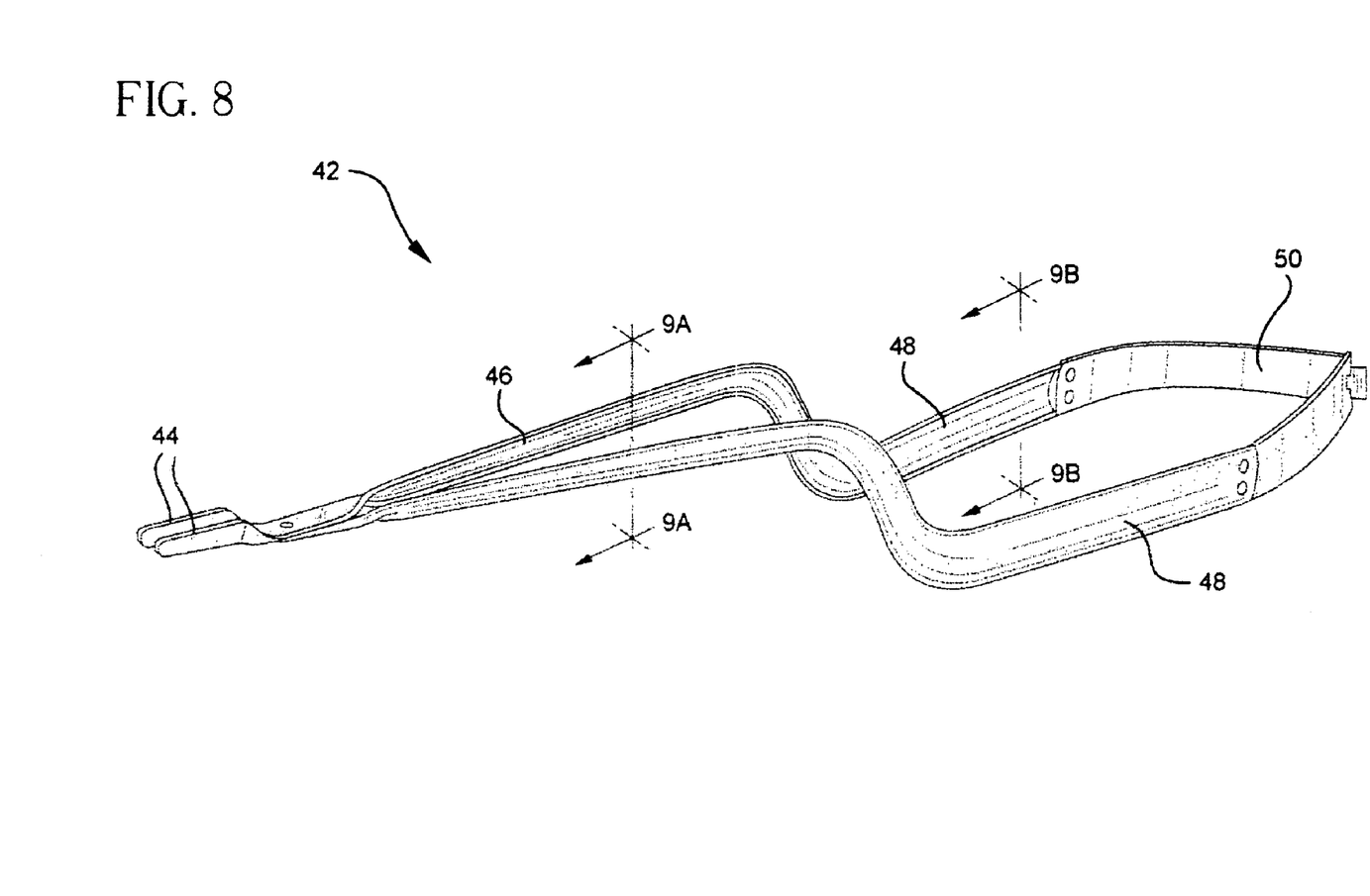
FIG. 8 is a perspective view of a surgical forceps constructed in accordance with the present invention.
Figure 9A:
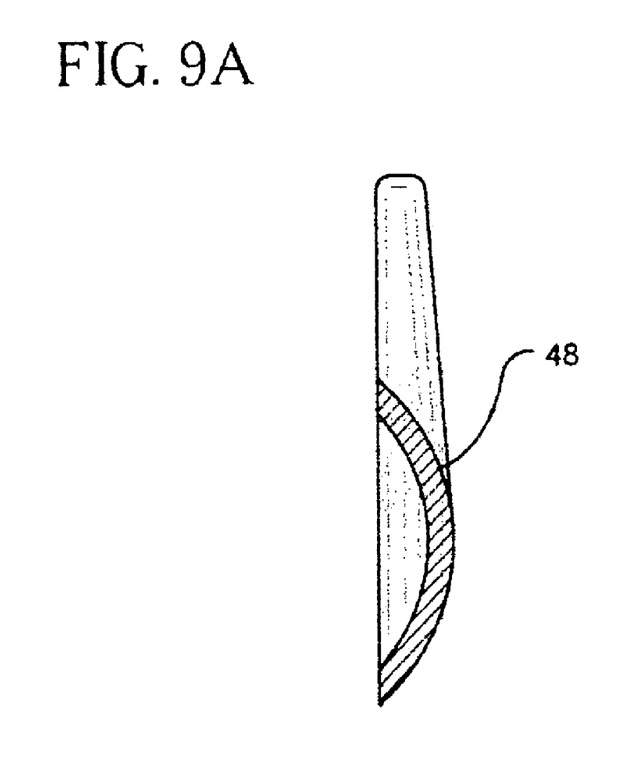
FIG. 9 is a sectional view of FIG. 8.
Figure 9B:
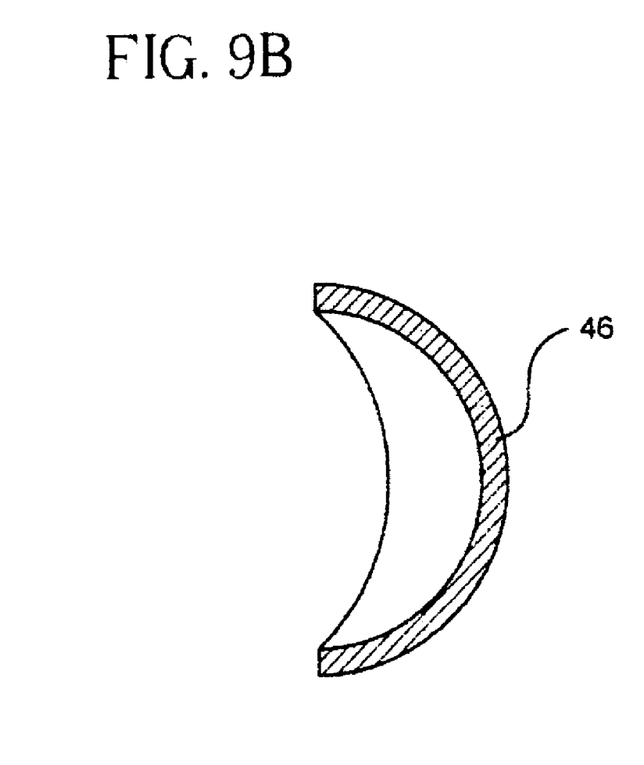

FIG. 8 shows a low profile forceps similar in construction to the scissors shown in FIG. 3. The forceps is referred to generally by the reference numeral 42 and has a pair of platforms 44, shanks 46, handles 48, and interconnected flexible bands 50. FIGS. 9a and 9b shows cross-sections through the handle and shanks respectively. It should be noted that the shanks have a much greater curvature than the handle curvature. The shanks can be of any curvature but preferably at least 180°. Consequently, greater beam strength is afforded this instrument permitting the entire force exerted at the handle being transmitted to the platforms of the forceps thereby sustaining the grip of the platforms by the user when the handle is grasped.

Figure 10:
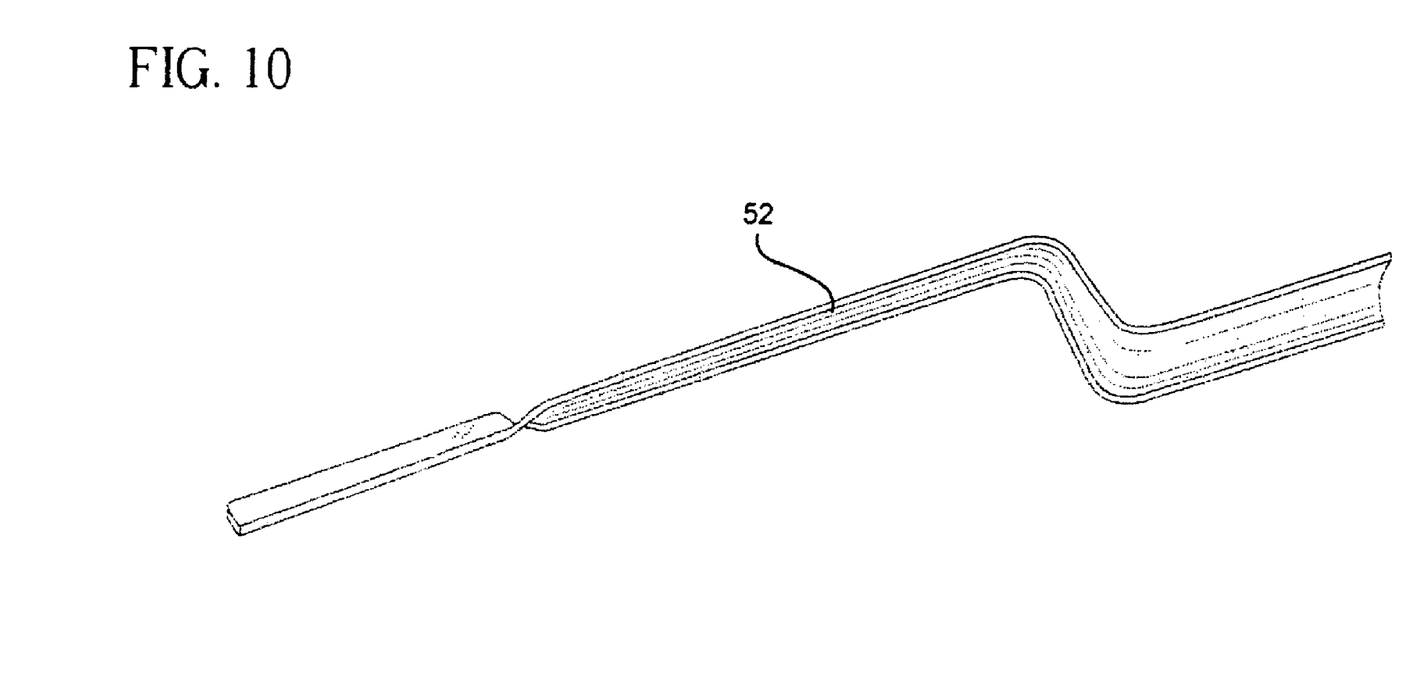
FIG. 10 is a perspective view of the stamped blank for the present improved surgical scissors.

FIG. 10 shows a blank 52 for the present surgical instrument that is fabricated by a stamping method instead of being machined out of metal stock or drop forged. This is a more economical method of manufacture but still results in an effective and precise instrument.

While it has been shown and described two embodiments of the present invention, it will be understood that those skilled in the art may make various changes in form and details of the instruments illustrated without departing from the true spirit of the invention.

What is claimed is:

1. An elongated, low profile surgical scissors constructed of medical grade flexibility resilient material for use where the operative fields are reduced comprising: a pair of handle parts, a pair of cutting blades, a pair of curved shanks connecting said blades to one end of said handle parts, a pair of flexible bands interconnected at one end and affixed at the other ends of said handle parts, and the curved shank having a convexity or concavity for greater beam strength of the scissors whereby the force applied to the handle parts is transferred to the blades without being diminished.

2. An elongated, low profile surgical scissors as claimed in claim 1 wherein said handle parts are convex having a convexity that is substantially less than the convexity of said shanks.

3. A surgical scissors as claimed in claim 1 where said scissors is fabricated of a metal stamping.

4. An elongated, low profile surgical forceps constructed of medical grade flexibly resilient material for use when the operative fields are reduced comprising: a pair of handle parts, a pair of gripping platforms, a pair of flexible bands interconnecting at one end thereof, and affixed at the other ends of said handle parts and the curved shanks having a convexity resulting in greater beam strength whereby the force of the forceps applied to the handles is transferred to the blades without being diminished.

5. A surgical scissors as claimed in claim 4 wherein said forceps is fabricated of a heat-treatable stainless steel.

6. A surgical forceps as claimed in claim 4 wherein said forceps is fabricated of a non-heat treatable material.

7. An elongated, lower profiled surgical scissors for use in an operative field where the openings are greatly reduced comprising a pair of cutting blades, a pair of curved handle parts, a pair of rounded shanks connecting said cutting blades to said handle parts, a pair of flexible bands interconnected on one end, and affixed to said handle parts at the other ends, and the rounded shanks having a greater convexity of at least 180° whereby the force applied to the handles is transferred to the cutting blades without being diminished.

8. A surgical scissors as claimed in claim 7 wherein said scissors is fabricated of a non-heat treatable material.

9. A surgical scissors as claimed in claim 7 wherein said rounded shanks have a greater convexity than the convexity of said handle parts.

10. An elongated, low profile surgical scissors constructed of medical grade flexibility resilient material comprising: a pair of curved shanks having flat connecting pieces at each end of said shanks remote from said cutting blades, a pair of flexible shanks interconnected at one end thereof and affixed at the other end to said handle parts, said handle parts having different configurations and being interchangeably removable attached to said flat connecting pieces, and the curved shanks having a convexity for greater beam strength of the scissors whereby the force applied to the handle parts is transferred to the blades without being diminished.

11. A surgical scissors as claimed in claim 10 wherein said handle parts have a convex gripping surface.

* * * * *